United States Patent [19]

Yahr

[11] Patent Number: 4,820,290
[45] Date of Patent: Apr. 11, 1989

[54] PROPHYLATIC DEVICE

[76] Inventor: James H. Yahr, 2999 Regent St., Berkeley, Calif. 94705

[21] Appl. No.: 96,488

[22] Filed: Sep. 15, 1987

[51] Int. Cl.⁴ ............................................. A61F 5/44
[52] U.S. Cl. .................................. 604/349; 604/352; 604/353; 128/844
[58] Field of Search ........ 604/349, 328, 329, 349–353; 128/132 R, 138 R

[56] References Cited

U.S. PATENT DOCUMENTS 2,891,546  6/1959  Galloway ........................... 604/353
3,677,225  7/1972  Czirey ............................ 604/352 X Primary Examiner—Larry Jones
Attorney, Agent, or Firm—Bielen and Peterson

[57] ABSTRACT

An abbreviated condom adapted to fit over the head of the penis the condom having a thin impervious hood with an open end having a continuous sealed connection to a wide, relatively thicker elastic band, the band being designed to be positioned in the coronal sulcus to prevent leakage of fluids collected in the hood.

10 Claims, 1 Drawing Sheet

PROPHYLATIC DEVICE

BACKGROUND OF THE INVENTION

This invention relates to a prophylatic device or more specifically to a condom that is abbreviated in length and design to fit over the head of the penis. The construction of the invented device enables the condom to be installed on a pretumescent penis which is a feature of particular importance to men in their aging years or men having difficulty obtaining and sustaining an erection. The particular construction of the condom differs substantially from a conventional prophylatic device in that an abbreviated hood is connected to a wide soft band that is installed below the corona of the penis head. This construction feature at the end open of the condom prevents rolling of the sheath when confronted by the longitudinal or shear friction encountered during intercourse. Prior art devices featuring an abbreviated hood for encasing only the glans penis, a means to secure the hood in place that differs substantially from that devised by applicant. Such devices usually include a harness type structure that engages the shaft of the penis to retain the hood over the penis head. Further, no differentiation in the thickness of the material used for the harness and th material used for the hood is provided.

The construction of the conventional condom device that is most commonly used is that of a elongated closed end sleeve or sheath that is rolled to a disk configuration prior to placement over the penis. Because of the particular construction, the device must be installed over an erect penis to enable the sleeve to be unrolled down to the penis to ensure a fit that will not cause the condom to be dislodged during the preliminaries of intercourse. Furthermore, in using a conventional condom, care must be taken to withdraw the condom with the penis to prevent the condom from being dislodged within the vigina when withdrawing a flacid, post climatic sex organ.

The wide band coupled to the hood of applicant's device ensures against accidental dislodgements and provides a protective barrier for prophylatic and contraceptive purposes.

SUMMARY OF THE INVENTION

The prophylatic of this invention comprises an abbreviated condom having a thin impervious hood and a relatively thick peripheral band connected to the open perimeter of the impervious hood. The condom is dimension to be worn over the glans penis such that the hood encompasses the glans and the band seats around the coronal sulcus. The band is preferably integrally formed with the hood and elastic in nature to snugly conform to the diameter of the penis in both its partially erect and erect condition. Various configurations of the hood are proposed in order to capture the ejaculated semen or preventing seepage of semen under the band. For example a hood with a sac of configuration similar to that of conventional condoms may be employed to receive the ejaculate. Preferably, however, the hood is connected with the edge of the band distal from the end of the penis such that an annular receptacle is provided between the band and the hood.

The abbreviated condom device of tis invention provides both the prophylatic and contraceptive functions of a conventional condom. Because the majority of the penis shaft is exposed, the abbreviated condom provides for greater sensitivity. This may be of importance to those who have difficulty in obtaining an erection or maintaining an erection while attempting to install a conventional condom. These and other features will become apparent from a detailed consideration of the preferred embodiments as follows.

DETAILED DESCRIPTION OF THE PREFERRED EMBODIMENTS

Figure 1:
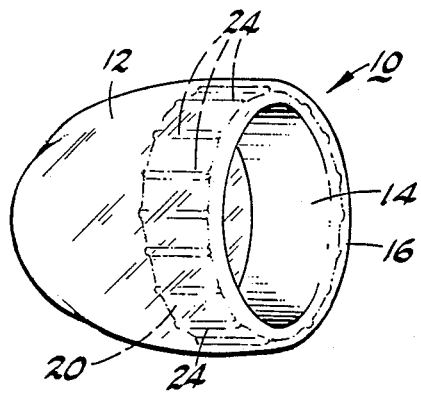
FIG. 1 is a perspective view of an abbreviated condom.
Figure 2:
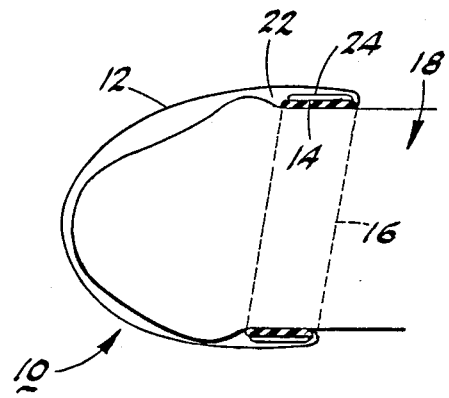
FIG. 2 is a schematic perspective of the condom in its installed position.

Referring now to FIG. 1, the preferred configuration of the abbreviated condom designated generally by the reference numeral 10 as shown. The condom 10 is constructed of two primary elements an impervious thin hood 12 and a relatively thick elastic band 14. In the preferred arrangement, the hood 12 connects to the band 14 at the peripheral edge 16 that is most distal from the end of the penis of the user 18 as shown in schematically in FIG. 2. In such construction, the hood 12 fits snugly over the glans of the penis and the band 14 forms a snug collar around the coronal sulcus such that the rim 20 of the band that is most proximate the end of the penis abuts the corona of the penis head or gland. With such construction, a loose annular pocket 22 is formed between the hood 12 and the band 14. This pocket provides for collection of ejaculate and relieves the band from fluid pressure that would otherwise result from a tight fit of the hood.

Figure 3:
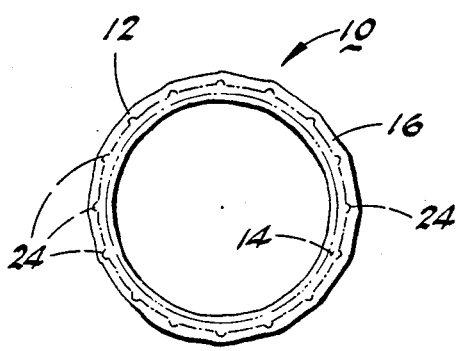
FIG. 3 is an end view of the condom FIG. 1.
Figure 4:
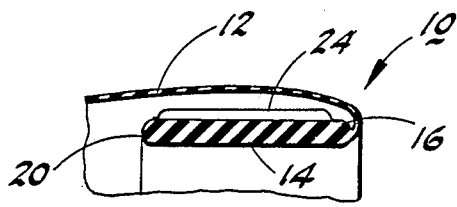
FIG. 4 is an enlarged, fragmented, cross-sectional view of a portion of a condom of FIG. 1.

The construction of the abbreviated condom 10 is such that the prophylatic and contraceptive functions are performed without using a sheath that encompasses the entire length of the male organ. As visible from the relative transparent hood 12 of the condom 10 in FIG. 1, the band includes a series of longitudinal ribs 24 which assist in maintaining the band around the neck of the penis without the band becoming dislodged by rolling of its edge into an annulus. While the band is elastic in nature, the material is soft and applies its elastic force gently without undue constriction. Use of the ribs 24 improves the anti-roll aspect which otherwise requires a slightly greater thickness to the band 14 than is required when the ribs are included. As shown in the end view of FIG. 3 the ribs 24 are uniformly spaced around the perimeter of the band 14 and are located within the outer sheath of the hood 12. Preferably, as shown in the enlarged sectional view of FIG. 4, hood 12 is integrally molded with the band 14. As shown, the ends of the band 16 and 20 have a rounded outer surface, again to assist in preventing the band from rolling at its distal and 16 when longitudinal shear forces are applied to the condom during intercourse.

Figure 5:
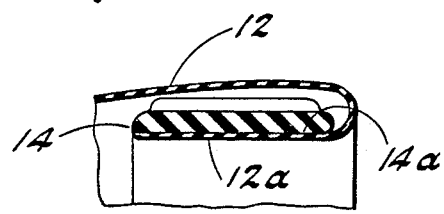
FIG. 5 is an enlarged, fragmented, cross-sectional view of an alternate construction of the condom of FIG. 1.

In FIG. 5 an alternate construction of the condom of FIG. 1 is illustrated. In this embodiment the band 14 includes an underlapping section 12a of the hood 12 that is circumferentially adhered to the inside surface 14a of the band 14. In this manner, fabrication of the individual elements, the hood and the band, may be accomplished independently and the elements united with a suitable adhesive or heat seal.

Figure 6:
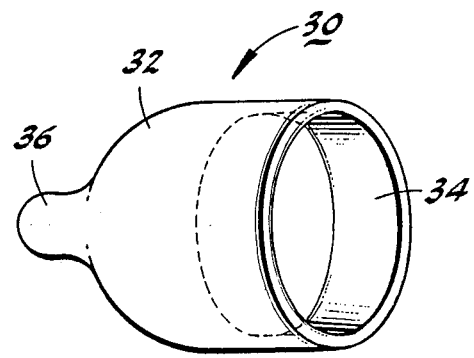
FIG. 6 is a perspective of an alternate embodiment of the abbreviated condom.
Figure 7:
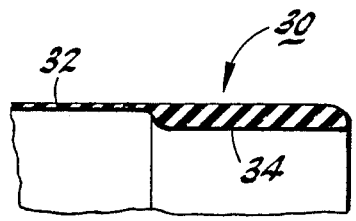
FIG. 7 is an enlarged, fragmented, cross-sectional view of a portion of the condom of FIG. 6.
Figure 8:
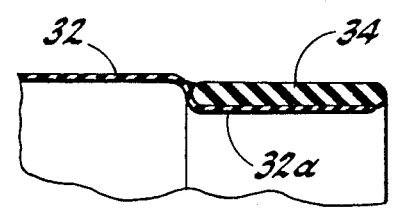
FIG. 8 is an enlarged, fragmented, cross-sectional view of an alternate construction of the condom of FIG. 6.

An alternate embodiment of the abbreviated condom is shown in FIG. 6 and designated generally by the reference numeral 30. In this embodiment the condom includes a hood 32 and a band 34 wherein the hood 32 is not folded back over the band 34 as in the primary embodiment. In the embodiment of FIG. 6, the hood 32 may optionally include a projecting nipple 36 which forms an end receptacle for collection and retention of the ejaculated semen. As shown in the enlarged cross-sectional view of FIG. 7, the sheath 32 is integrally fabricated with the band 34 in a single piece construction that may be formed by a molding process. The edges of the thicker band therefore are rounded again to prevent roll of the band which may cause accidental dislodgement or leakage of the contained fluid. The one piece construction of FIG. 7 may be modified as previously described and as shown in FIG. 8. In FIG. 8 the band 34 is sealed to an overlapping section 32a of the hood 32.

In both embodiments the preferred use is a soft fluid impervious latex material or a rubber material. The band should be easily stretchable such that the band is not unduly constricting when the male organ becomes enlarged. In some instances the band and the hood may be of different material. For example the hood may be comprised of natural membrane and the band of a man made substance and the materials joined by a suitable adhesive as shown in FIGS. 5 and 8.

The dimensions of the band could be approximately one-thirty second to one-sixteenth of an inch in thickness and one-quarter to one-half inch in width. The circumference can vary in size but should be in the range of 4 to 5 inches to comfortably fit a partially erect member. As noted, the ribs on the band are optional and are beneficial in minimizing the thickness of the band while retaining the necessary anti-roll characteristics.

The abbreviated condom can be inexpensively fabricated and has certain advantages over conventional condoms. The abbreviated condom can be placed on a tumescent penis allowing the band to expand as the diameter of the penis expands during excitation. This is an advantage to men particularly in their aging years since foreplay need not be interrputed at the moment of excitation and penis firmness for installation of a conventional condom.

While the foregoing embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. An abbreviated condom comprising a thin sheath formed in a hood with an open end, and, a relatively wide and thick elastic band, the open end of the hood having a continuous sealed connection with the band, the band forming an open end to the condom, the hood and band being constructed and sized to adapt to the end of a penis with the hood covering the glans and the band seating around the control sulcus and providing a seal for retaining fluid received in the hood, wherein the relatively wide and thick band is at least three magnitudes wider than it is thick and forms a continuous roll-preventing perimeter at the open end of the condom.

2. The condom of claim 1 wherein the band has a first edge locatable adjacent the corona of a user's penis and a second edge displaced from the corona when the condom is installed, the open end of the hood being joined to the second edge of the band.

3. The condom of claim 2 wherein the band and the hood are of a unitary construction.

4. The condom of claim 2 wherein the band has an outer surface and raised parallel ribs displaced around the outer surface for preventing the band from rollup.

5. The condom of claim 2 wherein the hood is sized to form an annular pocket between the band and the hood for receiving fluid.

6. The condom of claim 2 wherein the open end of the hood is joined to the edge of the band by a sealing means.

7. The condom of claim 1 wherein the band has a first edge locatable adjacent the corona of a user's penis and a second edge displaced from the corona when the condom is installed, the open end of the hood being joined to the first edge of the band.

8. The condom of claim 6 wherein the band and the hood and of a unitary construction.

9. The condom of claim 6 wherein the hood is joined to the edge of the band by a sealing means.

10. The condom of claim 6 wherein the hood has an end nipple forming a sac for receiving fluid.

* * * * *